(12) United States Patent
Storz et al.

(10) Patent No.: US 7,596,454 B2
(45) Date of Patent: Sep. 29, 2009

(54) METHOD FOR SEPARATING DETECTION CHANNELS OF A MICROSCOPE SYSTEM

(75) Inventors: Rafael Storz, Heidelberg (DE); Holger Birk, Meckesheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 728 days.

(21) Appl. No.: 10/822,428

(22) Filed: Apr. 12, 2004

(65) Prior Publication Data

US 2004/0209300 A1 Oct. 21, 2004

(30) Foreign Application Priority Data

Apr. 17, 2003 (DE) ................ 103 17 669

(51) Int. Cl.
*G06F 19/00* (2006.01)
(52) U.S. Cl. ...................................... 702/27
(58) Field of Classification Search ............. 702/19, 702/27
See application file for complete search history.

(56) References Cited

U.S. PATENT DOCUMENTS

2002/0109079 A1  8/2002  Engelhardt et al.
2003/0008364 A1*  1/2003  Wang et al. .............. 435/173.9
2003/0155494 A1  8/2003  Olschewski

FOREIGN PATENT DOCUMENTS

DE  10006800  8/2001
DE  10206979  8/2003

OTHER PUBLICATIONS

Lybarger et al. "Dual-Color Flow Cytometric Detection of Fluorescent Proteins Using Single-Laser (488-nm) Excitation." Cytometry (1998) vol. 31, pp. 147-152.*

* cited by examiner

*Primary Examiner*—Jerry Lin
(74) *Attorney, Agent, or Firm*—Houston Eliseeva LLP (57) ABSTRACT

A method for separating detection channels is disclosed, a sample (15) being equipped with at least two different fluorescent dyes. Firstly the emission spectrum of at least two fluorescent dyes is ascertained. From the emission spectra, the separation points of the wavelength and of the individual detection channels are determined. Lastly, adjustment of the separation of the at least two channels is accomplished on that basis.

16 Claims, 8 Drawing Sheets

METHOD FOR SEPARATING DETECTION CHANNELS OF A MICROSCOPE SYSTEM

RELATED APPLICATIONS

This application claims priority of the German patent application 103 17 669.1 which is incorporated by reference herein.

FIELD OF THE INVENTION

The invention concerns a method for separating detection channels of a microscope system.

BACKGROUND OF THE INVENTION

German Patent Application DE 100 06 800.6 discloses an apparatus (SP module) for selecting and detecting at least one spectral region of a spectrally spread light beam. Selection means that are embodied as sliders are provided in the spread-out light beam so as thereby to direct portions of the spread-out light beam to different detectors. Other suitable selection means for selecting the spectral region are also possible, for example micromirror arrays. The signals of the detectors are then used for image generation, the image quality depending in particular on the position of the sliders. The user must adjust the sliders in accordance with the position of the various emission spectra of the fluorescent dyes present in the sample. This is time-consuming for the user, and requires a good knowledge of the emission spectra of the various fluorescent dyes.

The German Patent Application DE 102 06 979.4 shows the general construction of a scanning microscope for user training. This user training allows a user to learn the setting operations for a scanning microscope without requiring a specimen or sample for that purpose during the entire learning phase. A software module that is interactively embodied is connected to the scanning microscope. The operating principle of an SP module is simulated in the specific interactive software module; i.e. spectral bands of several fluorescent dyes from the data set are separated, accumulated, combined into different channels, and displayed in multiple colors. All the capabilities of the software of a confocal scanning microscope are thus taken into account. The software does not, however, enable automatic separation, during examination of a specimen, of the various emission spectra of the fluorescent dyes in terms of the detection channels that are provided.

SUMMARY OF THE INVENTION

It is the object of the invention to create a method with which the various detection channels present in a microscope system are adjusted in such a way as to make possible an unequivocal and automatic separation of the emission spectra of the fluorescent dyes present in a sample.

The stated object is achieved by a method for separating detection channels, comprising the steps of:
a) providing a sample which is equipped with at least two fluorescent dyes
b) ascertaining an emission spectrum of the at least two fluorescent dyes, wherein the sample being excitable with different wavelengths and the number of different wavelengths is not exceeding the number of fluorescent dyes provided in the sample;
c) determining separation points of the emission spectrum in terms of wavelength, in order to allocate the corresponding portion of the emission spectrum to a specific channel in each case and to sense it with that channel; and
d) adjusting the separation of the at least two channels in such a way that the portions of the entire emission spectrum ascertained on the basis of the separation points are conveyed respectively to different channels for detection.

It is advantageous that the separation points of the portions of the emission spectrum are defined by the intersection points of the individual spectra of each fluorescent dye provided in the sample. Additionally, the separation points of the portions of the emission spectrum are ascertained by obtaining the difference between the measured emission spectrum of the biological sample and an emission spectrum at one excitation wavelength.

From the difference between the measured emission spectrum of the biological sample and an emission spectrum at one excitation wavelength, the integral of the square of the absolute value is obtained, and the separation points are determined by way of the minimum of the integral.

The detection of the one respective channel is performed with at least one detector element. Moreover the detector element comprises several detector elements grouped together. The at least one detector element can be configured as a photomultiplier.

A selection means is provided for adjusting the separation of the at least two channels. The selection means can be configured a micromirror array. The selection means can be as well a SP module. The SP module encompasses a mirror stop arrangement with which, on the basis of the ascertained separation points, the mirror stop arrangement is adjusted in such a way that each of the wavelength regions defined by the separation points is allocated respectively to one individual channel.

Further advantageous embodiments of the invention may be inferred from the dependent claims.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
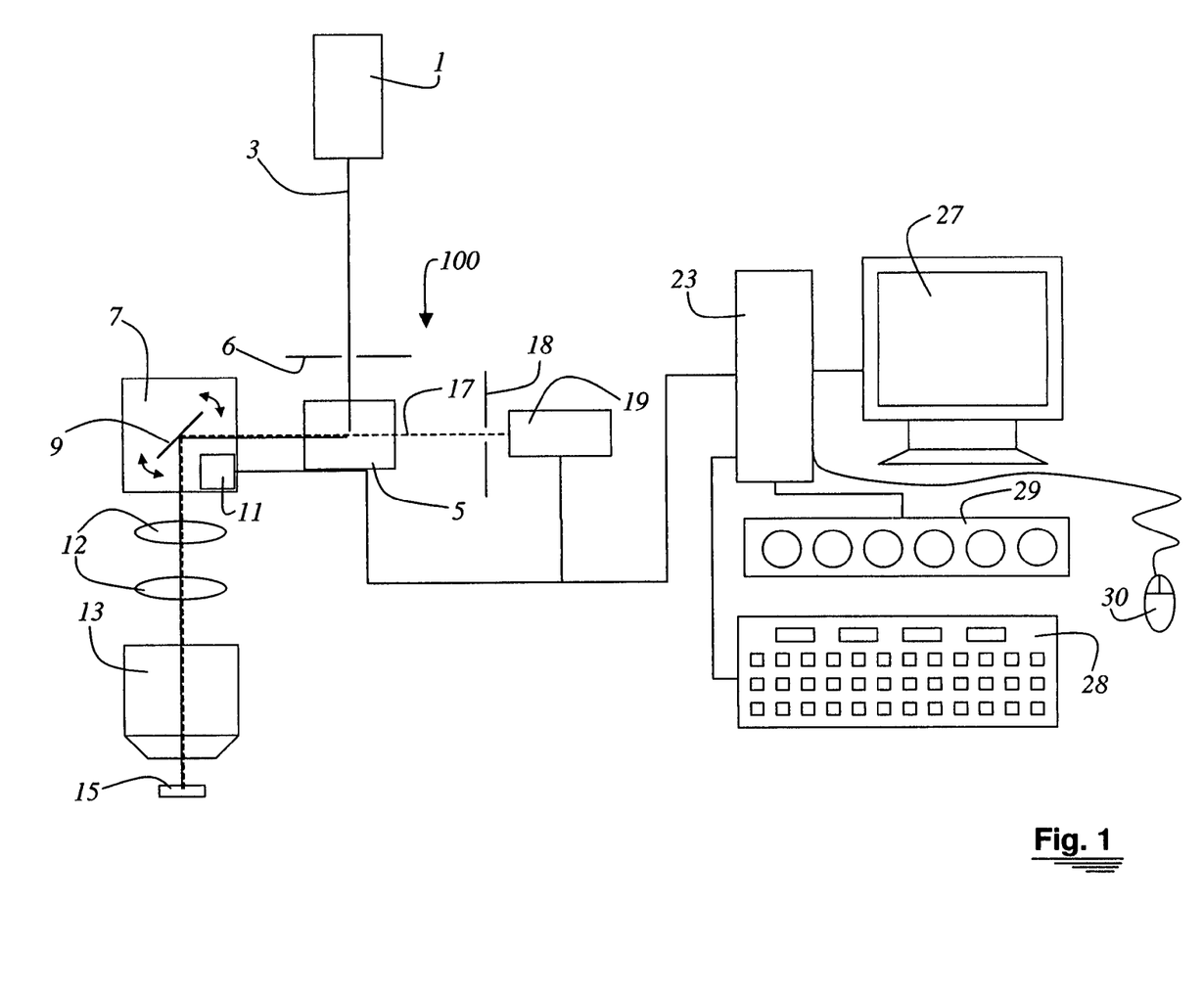
FIG. 1 shows a schematic exemplary embodiment of a confocal scanning microscope.

FIG. 1 schematically shows the exemplary embodiment of a confocal scanning microscope 100. This is not, however, to be construed as a limitation of the invention. It is sufficiently clear to one skilled in the art that the invention can also be implemented with a conventional scanning microscope or microscope system. Illuminating light beam 3 coming from at least one illumination system 1 is directed by a beam splitter or a suitable deflection means 5 to a scanning module 7. Illuminating light beam 3 can be made up of several excitation wavelengths with which the various dyes present in a sample are excited. Before illuminating light beam 3 strikes deflection means 5, it passes through an illumination pinhole 6. Scanning module 7 encompasses a gimbal-mounted scanning mirror 9 that guides illuminating light beam 3, through a scanning optical system 12 and a microscope optical system 13, over or through a sample 15 equipped with at least two fluorescent dyes. With non-transparent samples 15, illuminating light beam 3 is guided over the sample surface. With biological samples 15 (preparations) or transparent samples, illuminating light beam 3 can also be guided through sample 15. This means that different focal planes of sample 15 are scanned successively by illuminating light beam 3. Connected to scanning module 7 is a position sensor 11 that determines the position data of the acquired image data. Subsequent combination of the position data and image data then yields a two- or three-dimensional frame (or image) of sample 15. Illuminating light beam 3 coming from illumination system 1 is depicted as a solid line. The light proceeding from sample 15 defines a detected light beam 17. The latter travels through microscope optical system 13, scanning optical system 12 and via scanning module 7 to deflection means 5, passes through the latter, and travels through a detection pinhole 18 onto at least one detector 19 that encompasses at least two channels. Each of the channels can be embodied as a photomultiplier. It is clear to one skilled in the art that other detection components, for example diodes, diode arrays, photomultiplier arrays, CCD chips, or CMOS image sensors, can also be used. Detected light beam 17 proceeding from or defined by sample 15 is depicted in FIG. 1 as a dashed line. Electrical detected signals proportional to the power level of the light proceeding from sample 15 are generated in detector 19. Since light of not only one wavelength is emitted from sample 15, it is advisable to insert, in front of the various channels of the at least one detector 19, a selection means for the spectrum proceeding from sample 15. The data generated by detector 19 are forwarded to a computer system 23. At least one peripheral device 27 is associated with computer system 23. The peripheral device can be, for example, a display on which the user receives instructions for separating the spectrum proceeding from sample 15. Also depicted on the display is, for example, a user interface such as the one shown, for example, in FIG. 3. Additionally associated with computer system 23 is an input means that comprises, for example, a keyboard 28, an adjusting apparatus 29 for the components of the microscope system, and a mouse 30.

Figure 2:
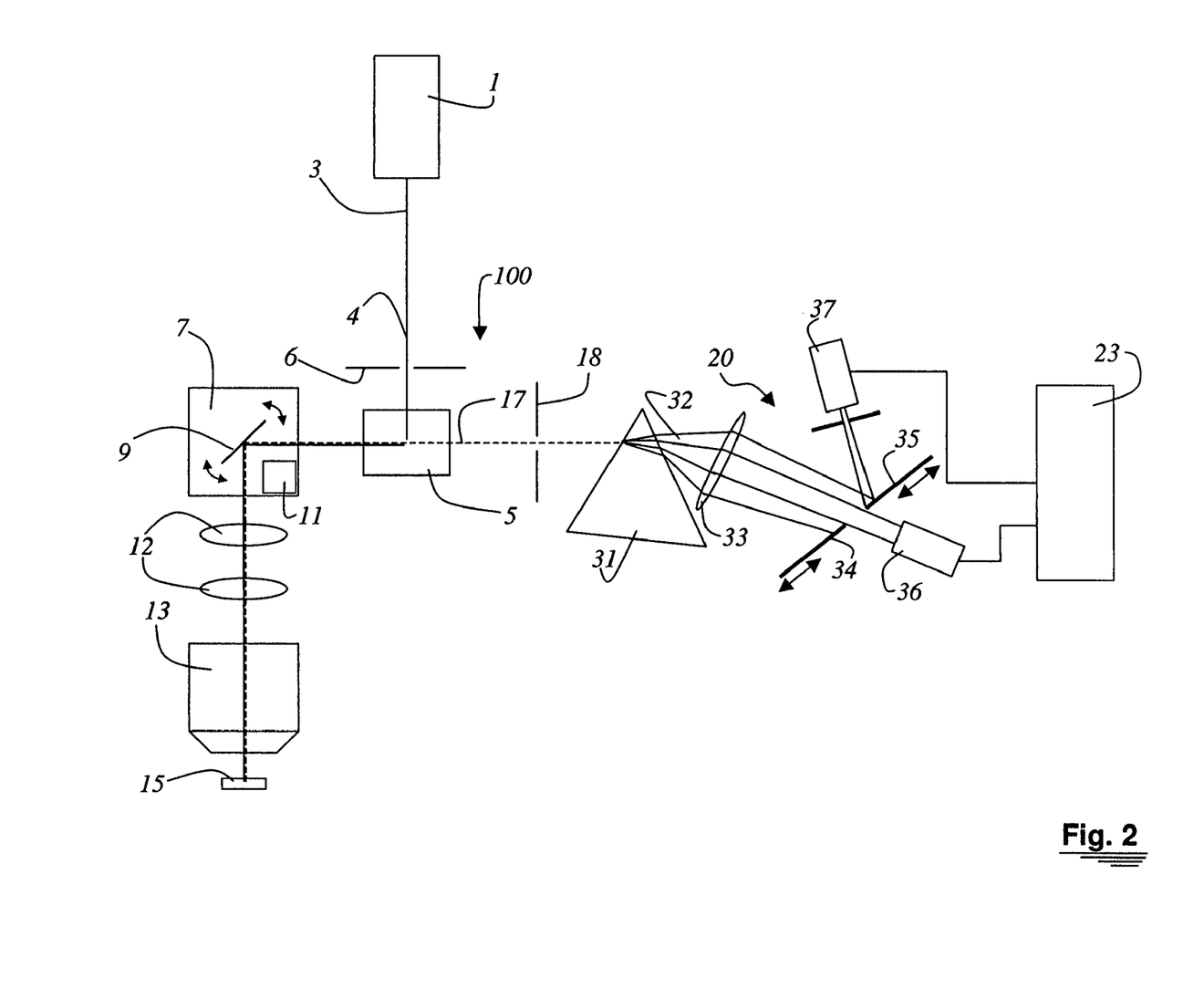
FIG. 2 shows an embodiment of a scanning microscope in which an SP module is arranged, as selection means, in front of the at least one detector.

FIG. 2 shows the embodiment of a scanning microscope in which an SP (spectral photometer) module 20 is arranged, as selection means, in front of the at least one detector 19. Other selection means, for example a micromirror array, are also conceivable. All other elements shown in FIG. 2 conform to those in FIG. 1, so they need not be mentioned again in the description of FIG. 2. SP module 20 (FIG. 2) acquires a complete lambda scan; i.e. for each sample point, all wavelengths proceeding from sample 15 are recorded. The data are transferred to computer system 23 and can then be presented on display 27 in a manner that can be determined by the user. Detected light beam 17 is spatially spectrally divided by a prism 31. A further possibility for spectral division is the use of a reflection grating or transmission grating. The spectrally divided light fan 32 is focused by focusing optical system 33, and then strikes a mirror stop arrangement 34, 35. Mirror stop arrangement 34, 35, the means for spectral spatial division (prism 31), focusing optical system 33, and detectors 36 and 37 are together referred to as SP module 20 (or the multi-band detector). As is evident from FIG. 2, a desired portion of the spectrum can be selected by means of mirror stop arrangement 34, 35. For that purpose, mirror stop arrangement 34, 35 in SP module 20 is correspondingly adjusted, depending on the separation that is ascertained, so as to direct only specific portions of the spectrum proceeding from sample 15 onto a respective individual detector. One portion of the divided light fan 32 of detected light beam 17, encompassing only light of the preselected spectral region, passes through mirror stop arrangement 34, 35 and is detected by detector 36, which is embodied as a photomultiplier. Another portion of the divided light fan 32 is reflected at mirror stop arrangement 35 and arrives at detector 37, which is likewise embodied as a photomultiplier. Mirror stop arrangements 34, 35 are displaceable in the directions illustrated by the double arrows, so that the spectral detection regions of the light conveyed to detectors 36, 37 are continuously adjustable. It is possible, although not depicted for reasons of clarity, also to install further detectors and to associate them with further mirror stops. In detectors 36, 37, electrical detected signals proportional to the power level of detected light beam 17 of the respective spectral region proceeding from sample 15 are generated, and are associated in computer system 23 with the position signals sensed in the beam deflection device by means of a position sensor.

Figure 3:
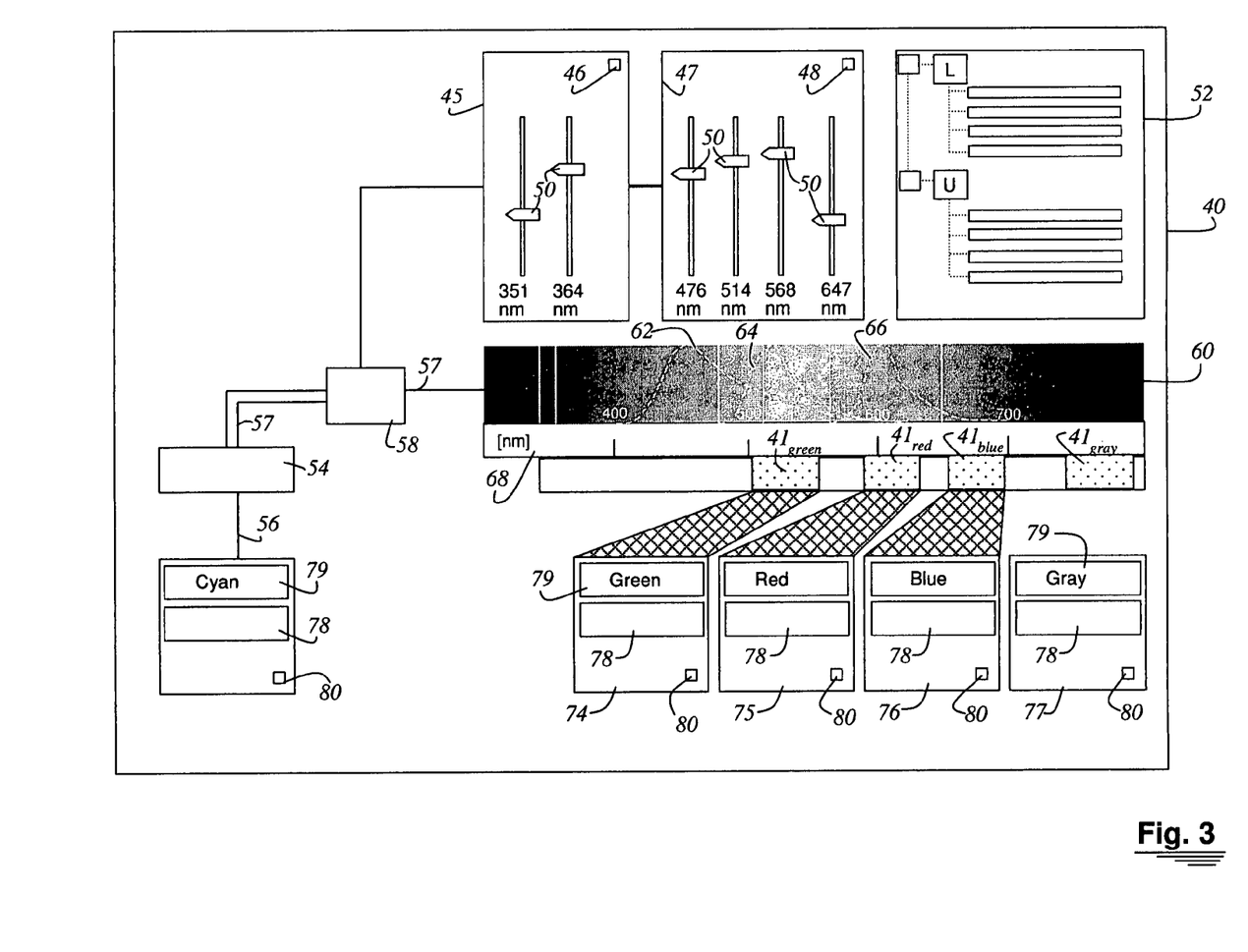
FIG. 3 shows a schematic embodiment of a user interface with which the user can adjust a number of desired channels.

FIG. 3 depicts part of a schematic embodiment of a user interface 40 with which the user can adjust a number of desired channels. The best setting is recommended to the user by the system. On the basis of the recommendation, selection sliders $41_{green}$, $41_{red}$, $41_{blue}$, or $41_{gray}$ are adjusted on user interface 40 for that purpose by the user, in accordance with the recommendation. The displacement by the user results in a corresponding displacement of mirror sliders 34 and 35 in SP module 20. The adjustment or displacement of the mirror sliders can also be accomplished automatically on the basis of the channel separation calculated by computer system 23.

The calculated data of the channels are displayed to the user on display 27; all possible presentation modes (overlay, volume rendering, etc.) can be incorporated into the depiction. To achieve the presentation on display 27, simulator is connected to computer system 23 in FIG. 1. Without stressing specimen 15 (thermally, with radiation, etc.), the user can continue for an appropriate period of time until he is satisfied with the image depicted on display 27. Pressing a key saves the setting and makes it available, as a filter macro or setting macro of SP module 20, for further work with the same specimen 15 or similar specimens. The scanning microscope is also schematically illustrated in the portion of user interface 40 depicted in FIG. 3, and a plurality of setting possibilities are made available to the user. In the embodiment described, a first laser 45 and a second laser 47 are provided, both schematically depicted as a box. First laser 45 is, for example, an argon UV (ArUV) laser that emits light of a first wavelength of 351 nm and light of a second wavelength of 364 nm. Second laser 47 is, for example, an argon-krypton (ArKr) laser that emits light of a first wavelength of 476 nm, light of a second wavelength of 514 nm, light of a third wavelength of 568 nm, and light of a fourth wavelength of 647 nm. Provided in each box, for each of the available wavelengths, is a slide controller 50 with which the percentage of the respective wavelength contained in the laser output can be adjusted. Also provided in each box is an indicator 46, 48 which reports the operating state of the respective laser and/or with which the laser can be switched on or off. Depicted alongside the box for second laser 47 is a data structure 52 showing how data are stored in the memory of computer system 23. Additionally depicted schematically on the display are the sample and a light beam coming from lasers 45, 47, a light beam 56 transmitted by the sample, and a light beam 57 emanating from the sample in the direction of the illuminating light beam. The light beams are correspondingly directed by a schematically depicted beam deflection device 58. In FIG. 3 the light beam 57 coming from the sample points toward a representation of a spectrum 60. The lines emitted by first and second laser 45, 47 are plotted in spectrum 60. Also depicted in spectrum 60 are the intensity and the spectral position of light 57 reflected from sample 15. In the exemplary embodiment depicted here, a first intensity curve 62, a second intensity curve 64, and a third intensity curve 66 are depicted in spectrum 60. Provided below spectrum 60 is a scale 68 that serves as an orientation aid for selection sliders $41_{green}$, $41_{red}$, $41_{blue}$, or $41_{gray}$ arranged therebelow. Selection sliders $41_{green}$, $41_{red}$, $41_{blue}$, or $41_{gray}$ are moved on user interface 40 with the mouse or a similar means. A first detector 74, a second detector 75, a third detector 76, and a fourth detector 77 are depicted, again schematically as boxes, below selection sliders $41_{green}$, $41_{red}$, $41_{blue}$, or $41_{gray}$. An indicator for dye selection is provided in each box. Indicator 73 is configured as a drop-down indicator, so that the user can easily select a different fluorescent dye present in the sample. Further associated with each box is a color description 79 which indicates how the signals of the respective detector are being used for image generation on the display. The operating state of each detector is indicated in each box by way of an activatable click box 80. A fifth detector, which likewise comprises indicator 78 for the dye detected by detector, box 79 for the color description, and the activatable click box 80, is associated with the light transmitted by the sample.

Figure 4:
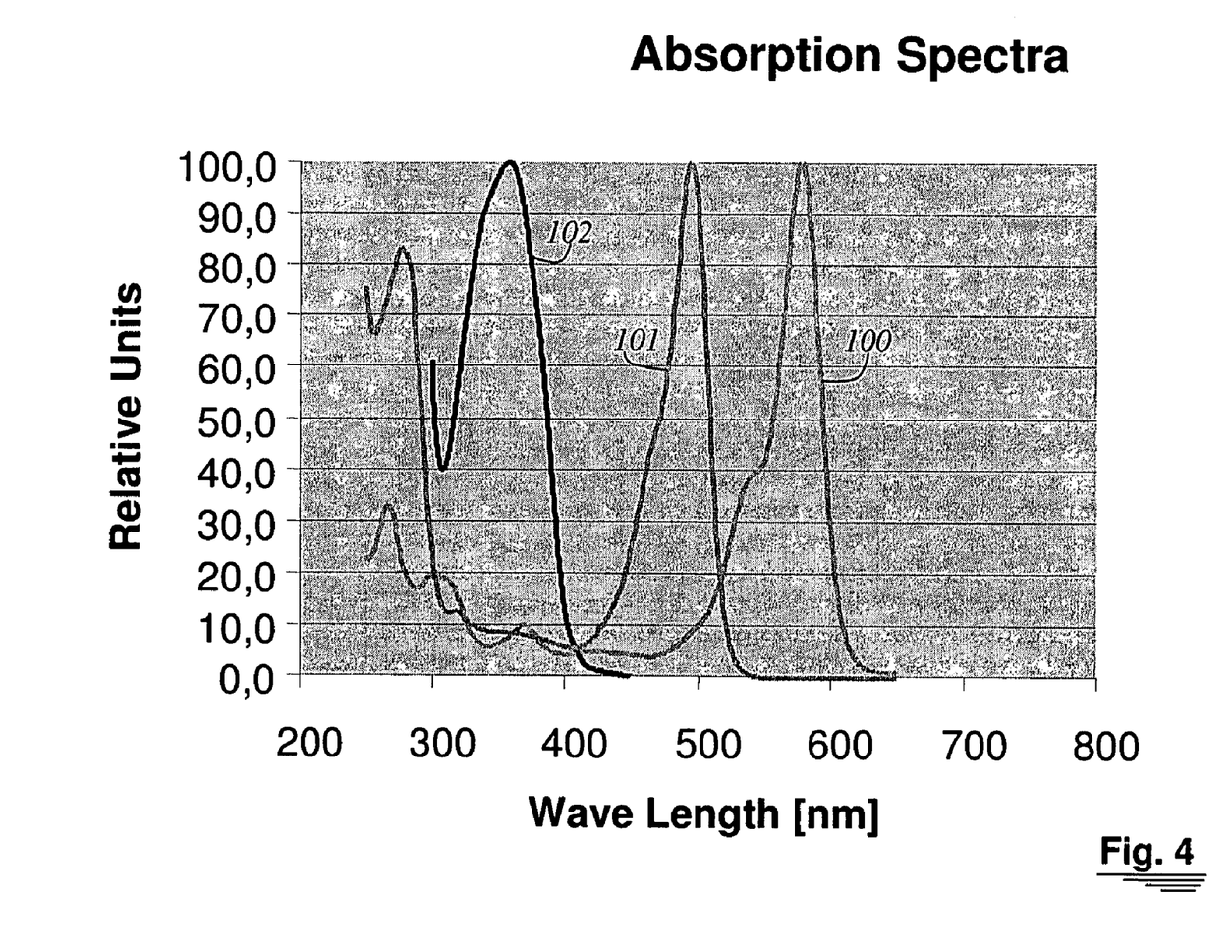
FIG. 4 shows the absorption spectra of three fluorescent dyes that are provided in the sample.

FIG. 4 shows the absorption spectra of three fluorescent dyes that are provided in sample 15, wavelength being plotted on the abscissa and relative units on the ordinate. First absorption spectrum 100 represents the fluorescent dye Texas Red. Second absorption spectrum 101 represents the fluorescent dye DAPI. Third absorption spectrum 102 represents the fluorescent dye FITC.

Figure 5:
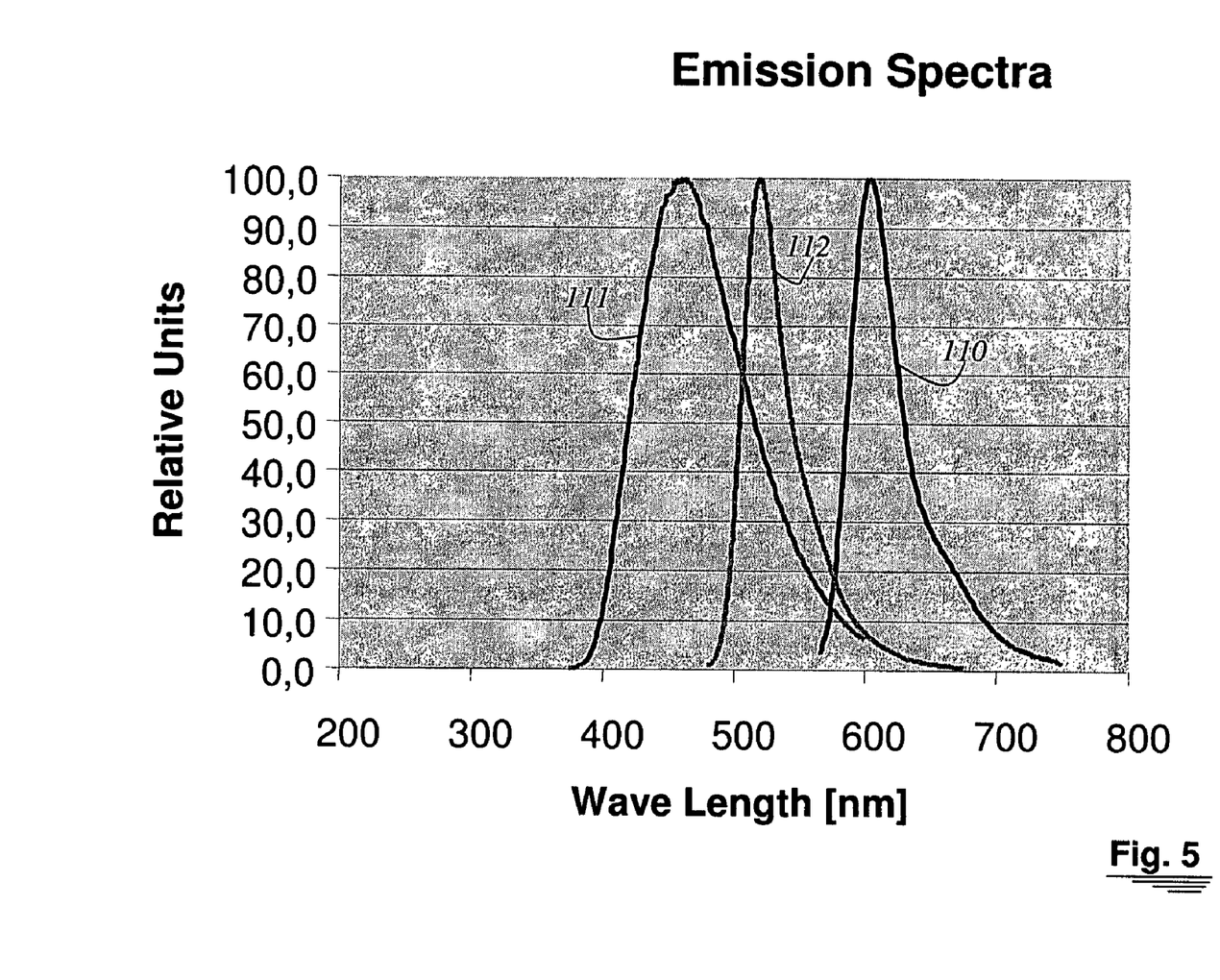
FIG. 5 shows the emission spectra of the three fluorescent dyes that are provided in the sample.

FIG. 5 shows the emission spectra of three fluorescent dyes that are provided in sample 15, wavelength being plotted on the abscissa and relative units on the ordinate. First emission spectrum 110 represents the fluorescent dye Texas Red. Second emission spectrum 111 represents the fluorescent dye DAPI. Third emission spectrum 112 represents the fluorescent dye FITC. The various emission spectra 110, 111, and 112 for the fluorescent dyes Texas Red, DAPI, and FITC, or also for other fluorescent dyes present in sample 15, are stored in a database that is implemented in computer system 23.

Figure 6:
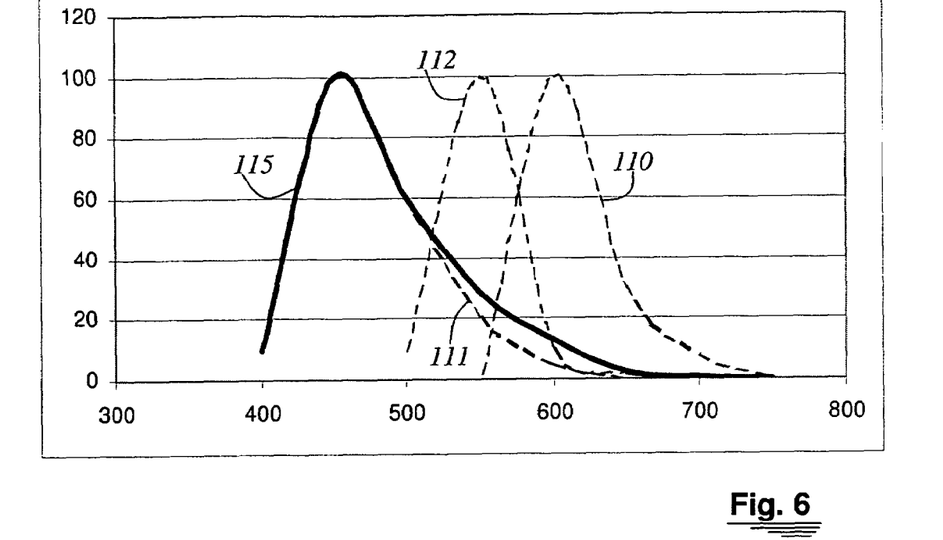
FIG. 6 shows the emissions of the fluorescent dyes provided in the sample upon excitation with a wavelength of 357 nm.

FIG. 6 shows emission 115 of the fluorescent dyes provided in sample 15 upon excitation with a wavelength of 357 nm, wavelength being plotted on the abscissa and relative units on the ordinate. First emission spectrum 110 represents the fluorescent dye Texas Red. Second emission spectrum 111 represents the fluorescent dye DAPI. Third emission spectrum 112 represents the fluorescent dye FITC. In this context, 100% of emission 115 is attributable to DAPI, 8% of emission 115 is contributed by FITC, and 7% of emission 115 is contributed by Texas Red.

Figure 7:
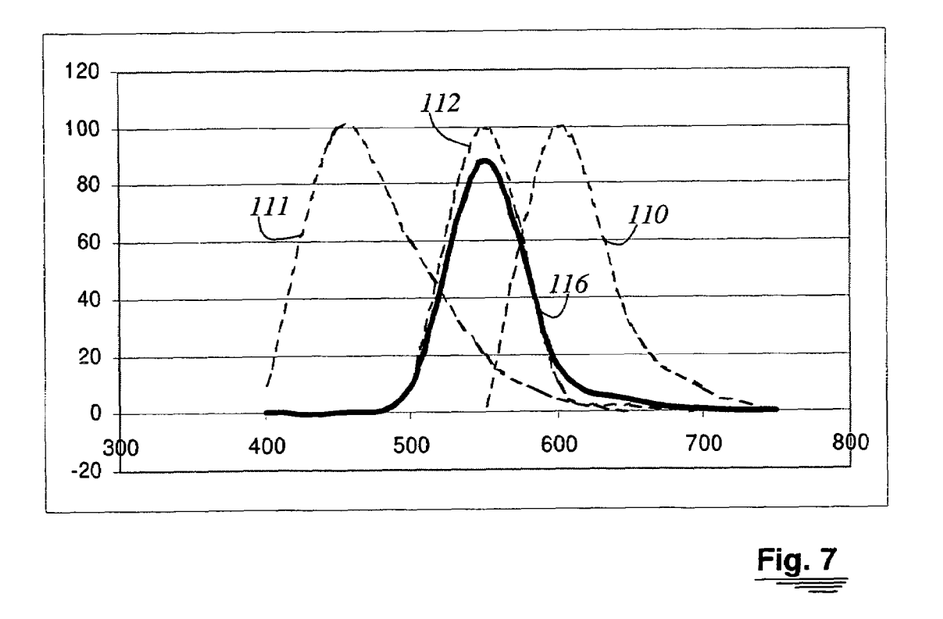
FIG. 7 shows the emissions of the fluorescent dyes provided in the sample upon excitation with a wavelength of 488 nm.

FIG. 7 shows emission 116 of the fluorescent dyes provided in sample 15 upon excitation with a wavelength of 488 nm, wavelength being plotted on the abscissa and relative units on the ordinate. First emission spectrum 110 represents the fluorescent dye Texas Red. Second emission spectrum 111 represents the fluorescent dye DAPI. Third emission spectrum 112 represents the fluorescent dye FITC. In this context, 0% of emission 116 is attributable to DAPI, 88% of emission 116 is contributed by FITC, and 7% of emission 116 is contributed by Texas Red.

Figure 8:
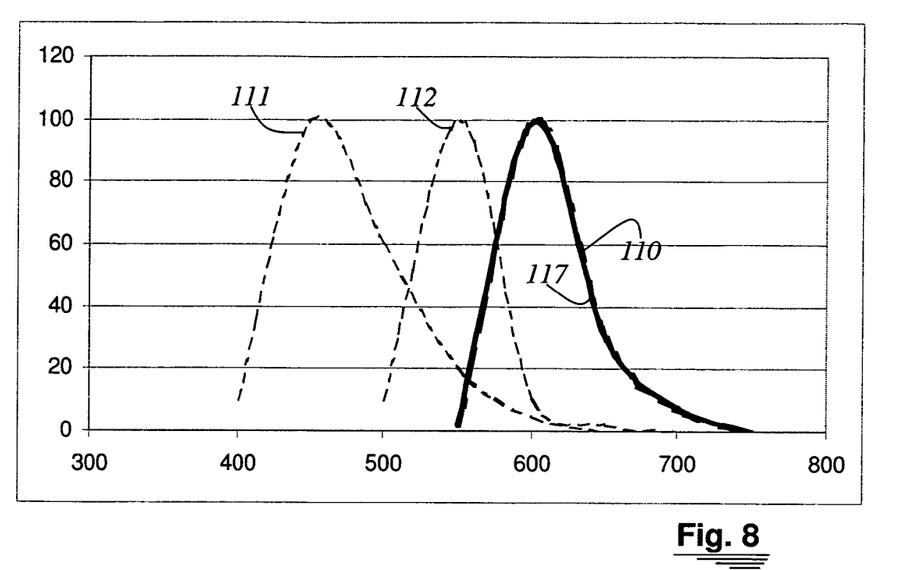
FIG. 8 shows the emissions of the fluorescent dyes provided in the sample upon excitation with a wavelength of 576 nm.

FIG. 8 shows emission 117 of the fluorescent dyes provided in sample 15 upon excitation with a wavelength of 576 nm, wavelength being plotted on the abscissa and relative units on the ordinate. First emission spectrum 110 represents the fluorescent dye Texas Red. Second emission spectrum 111 represents the fluorescent dye DAPI. Third emission spectrum 112 represents the fluorescent dye FITC. In this context, 0% of emission 117 is attributable to DAPI, 0% of emission 117 is contributed by FITC, and 99% of emission 117 is contributed by Texas Red.

Figure 9:
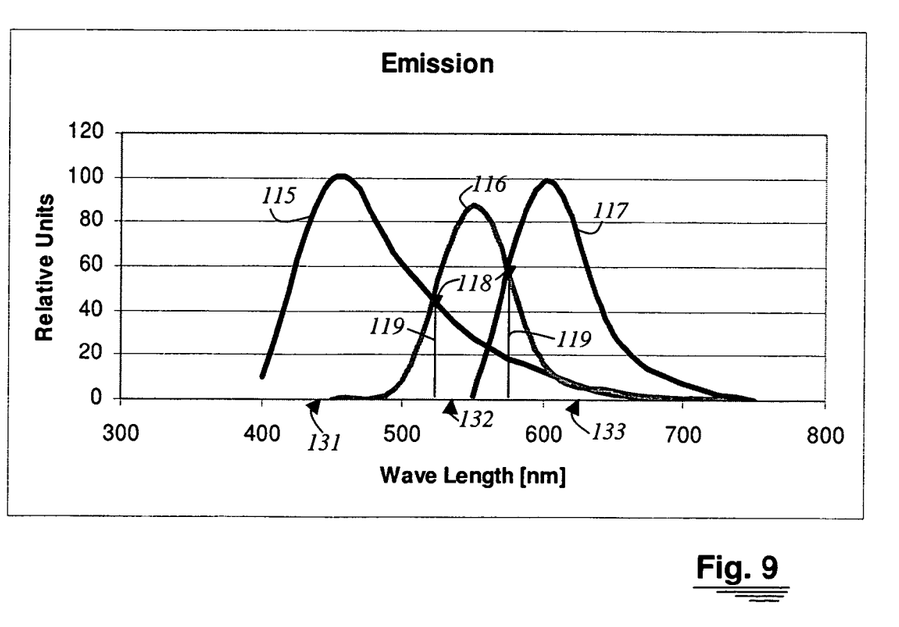
FIG. 9 shows the emissions of the fluorescent dyes provided in the sample upon excitation with the three different wavelengths of 357 nm, 488 nm, and 576 nm.

FIG. 9 shows, in a graph, all the emissions 115, 116, 117 of the fluorescent dyes provided in sample 15, for the various excitations. The spectra of the emissions depicted in FIG. 6, FIG. 7, and FIG. 8 are combined in one graphic depiction, wavelength being plotted on the abscissa and relative units on the ordinate. First emission 115 represents the excitation of the three fluorescent dyes provided in sample 15 for the 357 nm excitation. Second emission 116 represents the excitation of the three fluorescent dyes provided in sample 15 for the 488 nm excitation. Third emission 117 represents the excitation of the three fluorescent dyes provided in sample 15 for the 576 nm excitation. FIG. 9 depicts an embodiment for the determination of separation points 118 in order to allocate a certain portion of the emission spectrum to a certain channel. Separation points 118 are determined by projecting intersection points 119 of emissions 115, 116, and 117 onto the abscissa. This results in a separation, a first channel 131 encompassing the wavelength region from 400 to 520 nm, a second channel 132 the wavelength region from 520 to 580 nm, and a third channel 133 the wavelength region from 580 to 750 nm.

FIGS. 6 through 9 describe the conditions if all the dyes occur within the image region (pixels) of interest (co-localization). If all the dyes are not present simultaneously, the conditions become correspondingly simpler.

Figure 10:
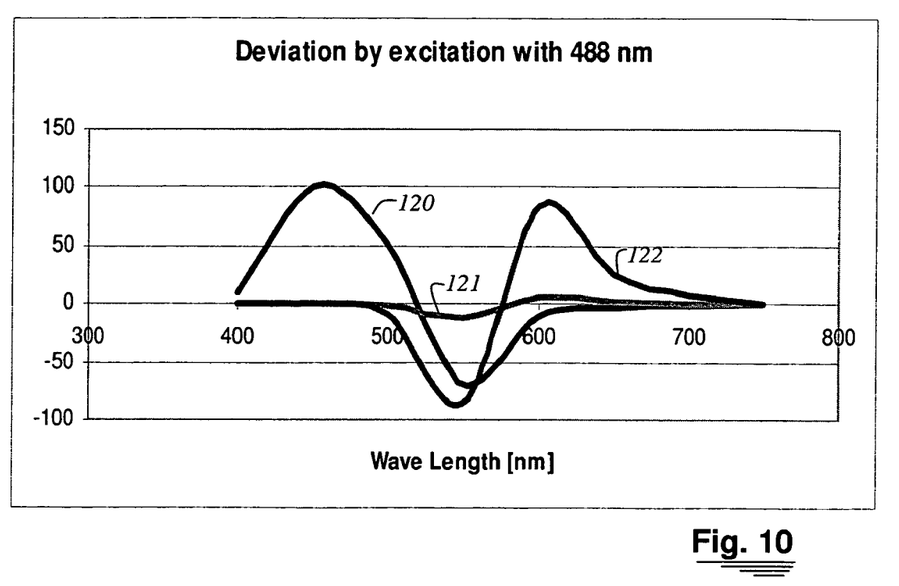
FIG. 10 shows the difference between the emission spectrum for one fluorescent dye provided in the sample and the measured emission spectra of the fluorescent dyes present in the sample, upon excitation with a wavelength of 488 nm.
Figure 11:
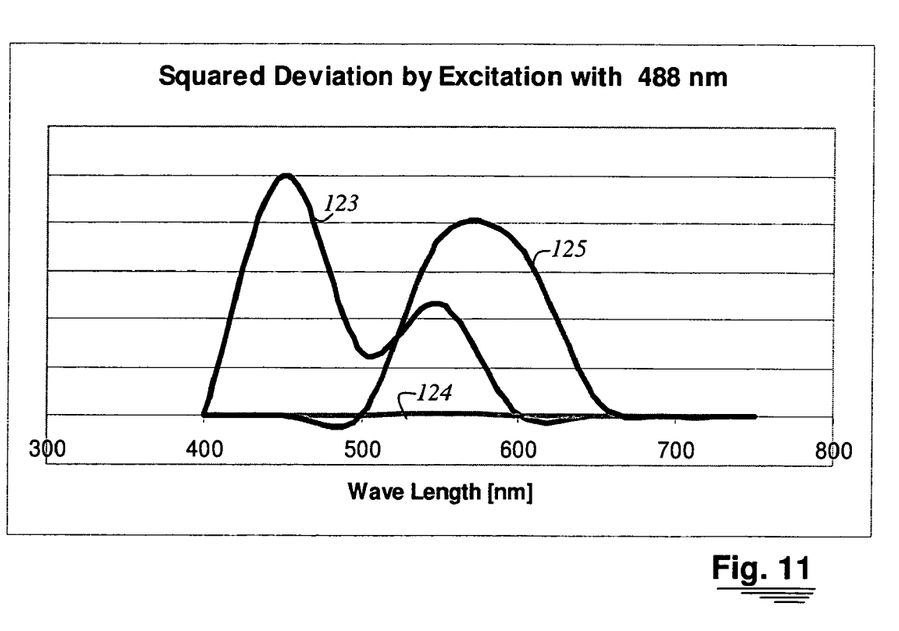
FIG. 11 shows the square of the difference between the emission spectrum for one fluorescent dye provided in the sample and the measured emission spectra of the fluorescent dyes present in the sample, upon excitation with a wavelength of 488 nm.

FIGS. 10 and 11 that follow concern the allocation and identification of measured dyes by comparison with reference spectra that, for example, are stored in the memory of computer system 23.

FIG. 10 shows the difference between the emission spectrum for one fluorescent dye provided in the sample and the emission spectrum of the fluorescent dyes present in the sample, upon excitation with a wavelength of 488 nm, wavelength being plotted on the abscissa and relative units on the ordinate. First difference spectrum 120 represents the difference between the emission spectrum of the fluorescent dye DAPI and the emission spectrum of the fluorescent dyes in the sample, upon excitation with a wavelength of 488 nm. Second difference spectrum 121 represents the difference between the emission spectrum of the fluorescent dye FITC and the emission spectrum of the fluorescent dyes in the sample, upon excitation with a wavelength of 488 nm. Third difference spectrum 122 represents the difference between the emission spectrum of the fluorescent dye Texas Red and the emission spectrum of the fluorescent dyes in the sample, upon excitation with a wavelength of 488 nm.

FIG. 11 shows the square of the difference between the emission spectrum for one fluorescent dye provided in the samples and the measured emission spectra of the fluorescent dyes present in the sample, upon excitation with a wavelength of 488 nm, wavelength being plotted on the abscissa and relative units on the ordinate. First square 123 is that of first difference spectrum 120 of the fluorescent dye DAPI. Second square 124 is that of second difference spectrum 121 of the fluorescent dye FITC. Third square 125 is that of third difference spectrum 122 of the fluorescent dye Texas Red. An allocation can easily be made in that the integral of the square of the absolute value (see FIG. 11) must be minimal. That is the case here for FITC.

Optimum setting of the wavelength regions for separation of the individual channels is described below.

A separation algorithm is applied by way of the transition into the hyperspace spanned by the channels used. The dyes are then described as linear combinations of the channels. Without limitation, the calculations are performed here using vectors normalized to unity, in accordance with the channel separation as e.g. in FIG. 9, where first channel 131 encompasses the wavelength region from 400 to 520 nm, second channel 132 the wavelength region from 520 to 580 nm, and third channel 133 the wavelength region from 580 to 750 nm.

The resulting integrals of the intensity distribution within these channels are then (0.80, 0.25, 0.09) for DAPI, (0.42, 0.49, 0.05) for FITC, and (0, 0.13, 0.33) for Texas Red. After projection onto the unit sphere and normalization, this yields the following vectors: (0.95, 0.30, 0.10) for DAPI, (0.65, 0.76, 0.08) for FITC, and (0, 0.37, 0.93) for Texas Red.

The selection criterion for this algorithm is then that the angles between the unit vectors of the dyes become maximal, corresponding to a maximum separation. As parameters, the limits for the detection bands are shifted. In mathematical terms, the sum of the squares of the absolute values of the scalar products is to be minimized in this operation, which is a conventional extreme-value task. It can be stated as a boundary condition for the limits of the wavelength regions or detection bands, for example, that the available spectral region be maximally utilized and the signal-to-noise ratio thus optimized.

For known dyes, the optimum detection bands can be calculated from the dye emission values, which can be stored in a memory of computer system 23. For dyes that are not yet known, the sequentially acquired spectra are used.

It is self-evident that the description of the method using the three fluorescent dyes cannot be construed as a limitation. A sample to be examined can be equipped with any number of fluorescent dyes. The method is independent of the use of specific fluorescent dyes.

The invention has been described with reference to a particular embodiment. It is self-evident, however, that changes and modifications can be made without thereby leaving the range of protection of the claims below.

What is claimed is:

1. A method for separating detection channels, comprising the steps of:
   providing a sample with at least two fluorescent dyes;
   exciting the at least two fluorescent dyes with light of different excitation wavelengths, wherein the number of different excitation wavelengths does not exceed the number of fluorescent dyes in the sample;
   obtaining a measured emission spectrum of the sample;
   determining wavelength separation points of the emission spectrum to allocate a corresponding portion of the measured emission spectrum to a corresponding detection channel; and
   conveying light from the sample into the different detection channels according to the separation points,
   wherein the separation points are determined by:
   finding a difference between an emission spectrum of one fluorescent dye of the at least two dyes present in the sample measured at a certain wavelength and a measured emission spectrum of the sample measured at the same wavelength;
   squaring the difference; and
   minimizing an integral of the square of the difference.

2. A method for separating detection channels, comprising the steps of:
   providing a sample with at least two fluorescent dyes;
   exciting the at least two fluorescent dyes with light of different excitation wavelengths, wherein the number of different excitation wavelengths does not exceed the number of fluorescent dyes in the sample;
   obtaining a measured emission spectrum of the sample;
   determining wavelength separation points of the emission spectrum to allocate a corresponding portion of the measured emission spectrum to a corresponding detection channel; and
   conveying light from the sample into the different detection channels according to the separation points,
   wherein the wavelength separation points of the portions of the emission spectrum are defined by intersection points of the individual spectra of each fluorescent dye in the sample.

3. The method as defined in claim 1, wherein detection in the corresponding detection channel is performed with at least one detector element.

4. The method as defined in claim 3, wherein the detector element comprises several detector elements grouped together.

5. The method as defined in claim 4, wherein signals of several detectors of a multi-anode photomultiplier are grouped together into one channel.

6. The method as defined in claim 3, wherein the at least one detector element is a photomultiplier.

7. The method as defined in claim 1, wherein adjusting the separation between at least two channels is done by a selection means.

8. The method as defined in claim 7, wherein the selection means is a micromirror array.

9. The method as defined in claim 7, wherein the selection means is a spectral photometer (SP) module.

10. The method as defined in claim 9, wherein the SP module comprises a mirror stop arrangement adjusted in such a way that each of the wavelength regions defined by the wavelength separation points is allocated, respectively, to one individual detection channel.

11. The method as defined in claim 1, wherein the wavelength separation points are determined by a computer system.

12. The method as defined in claim 11, wherein the data corresponding to the wavelength separation points are presented to a user on a display.

13. The method as defined in claim 12, wherein the user adjusts the mirror stop arrangement on the basis of the data presented on the display.

14. The method as defined in claim 11, further comprising automatically adjusting the mirror stop arrangement or the micromirror array is automatically adjusted in such a way that each wavelength region defined by the wavelength separation points is allocated to one its respective detection channel.

15. The method as defined in claim 1, further comprising detecting light in at least one detection channel with a detector.

16. The method as defined in claim 2, further comprising detecting light in at least one detection channel with a detector.

* * * * *